United States Patent
Cahill, Jr. et al.

(10) Patent No.: US 9,545,368 B2
(45) Date of Patent: Jan. 17, 2017

(54) SKIN CARE COMPOSITIONS HAVING CYCLIC DIESTERS AND METHODS THEREOF

(71) Applicant: THE CHEMOURS COMPANY FC LLC, Wilmington, DE (US)

(72) Inventors: William R Cahill, Jr., Hockessin, DE (US); Jessica Linda Reisack, Middletown, DE (US); Robert Ray Burch, Exton, PA (US); Jennifer Marie Altland, Lancaster, PA (US); Jeffrey Jon Horsager, Edina, MN (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/455,118

(22) Filed: Aug. 8, 2014

(65) Prior Publication Data

US 2015/0045421 A1 Feb. 12, 2015

Related U.S. Application Data

(60) Provisional application No. 61/864,172, filed on Aug. 9, 2013.

(51) Int. Cl.
| | | |
|---|---|---|
| *A61K 8/49* | (2006.01) | |
| *A61Q 19/00* | (2006.01) | |
| *A61K 8/31* | (2006.01) | |
| *A61K 8/37* | (2006.01) | |

(52) U.S. Cl.
CPC .............. *A61K 8/498* (2013.01); *A61K 8/31* (2013.01); *A61K 8/375* (2013.01); *A61K 8/4973* (2013.01); *A61Q 19/00* (2013.01); *A61Q 19/007* (2013.01); *A61K 2800/31* (2013.01); *A61K 2800/75* (2013.01)

(58) Field of Classification Search
CPC ... A61K 8/498; A61K 2800/75; A61Q 19/007
USPC ........................................................ 514/452
See application file for complete search history.

(56) References Cited

U.S. PATENT DOCUMENTS

| | | |
|---|---|---|
| 4,234,599 A | 11/1980 | Van Scott et al. |
| 5,385,938 A | 1/1995 | Yu et al. |
| 5,552,147 A | 9/1996 | Znaiden et al. |
| 5,610,199 A | 3/1997 | Cohen et al. |
| 5,648,380 A | 7/1997 | Martin |
| 5,686,083 A | 11/1997 | Chamness |
| 5,886,042 A | 3/1999 | Yu et al. |
| 5,939,085 A | 8/1999 | Jacobs et al. |
| 5,948,418 A | 9/1999 | Maes et al. |
| 2001/0016604 A1 | 8/2001 | Yu et al. |
| 2002/0051819 A1 | 5/2002 | Kuhner et al. |
| 2003/0017130 A1* | 1/2003 | Yu ............. A61K 8/347 424/78.03 |
| 2004/0161392 A1 | 8/2004 | Hansenne et al. |
| 2007/0010580 A1 | 1/2007 | De Paoli Ambrosi |
| 2008/0057088 A1 | 3/2008 | Blass et al. |
| 2008/0311231 A1 | 12/2008 | Modak et al. |
| 2009/0030059 A1 | 1/2009 | Miki et al. |
| 2009/0226541 A1 | 9/2009 | Scholz et al. |
| 2010/0172851 A1 | 7/2010 | Yu et al. |

FOREIGN PATENT DOCUMENTS

| | | |
|---|---|---|
| CN | 102078300 B | 6/2011 |
| EP | 0673642 B1 | 7/2000 |
| EP | 1795181 A1 | 6/2007 |
| JP | 63-091311 A | 4/1988 |
| JP | 10-114642 A | 5/1998 |
| JP | 10-120547 A | 5/1998 |
| JP | 2002-179528 A | 6/2002 |
| WO | 9621422 A1 | 7/1996 |
| WO | 0149273 A2 | 7/2001 |
| WO | 02091966 A1 | 11/2002 |

OTHER PUBLICATIONS

U.S. Appl. No. 14/455,115, filed Aug. 8, 2014.
Internet Webpage: www.makeuptalk.com/f/topic/101925-penetration-enhancer-dimethyl-isosorbide-dmi/(2010).

* cited by examiner

Primary Examiner — Kristin Vajda

(57) ABSTRACT

The present invention generally relates to topical skin care compositions having at least one cyclic diester. More specifically, the present invention relates to novel topical skin care compositions having at least one cyclic diester of an alpha hydroxy acid, and at least one polar non-aqueous solvent.

7 Claims, 1 Drawing Sheet

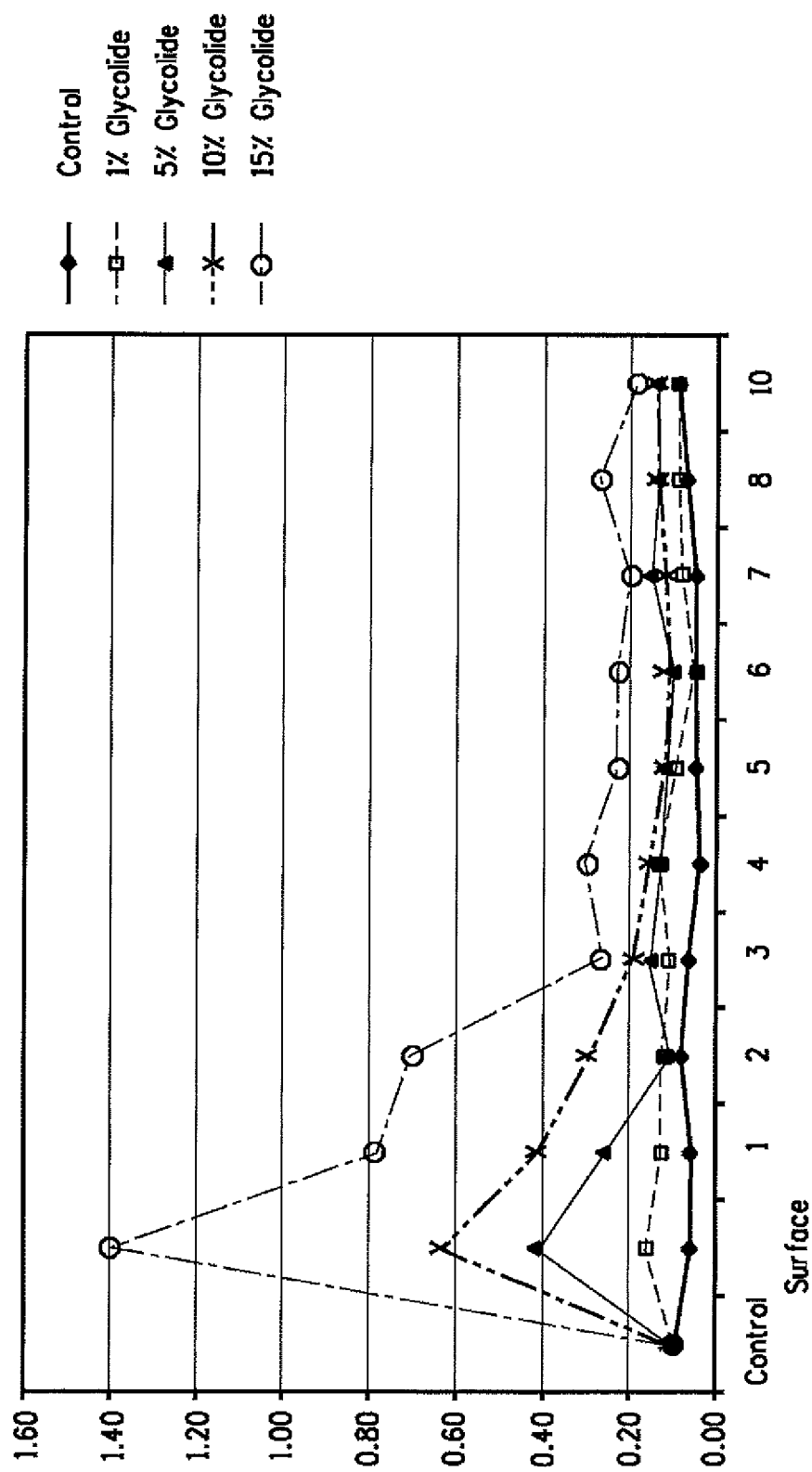

ical skin care compositions having at least one cyclic diester. More specifically, the present invention relates to novel topical skin care compositions having at least one cyclic diester of an alpha hydroxy acid, and at least one polar non-aqueous solvent.

BACKGROUND OF THE INVENTION

Alpha hydroxy acids ("AHAs") are known to be useful in skin care compositions for treating various skin conditions, including rhytids (i.e., wrinkles), xeroderma (i.e., dry skin), hyperkeratosis, ichthyosis, and discoloration. Specifically, AHAs that are short chain carboxylic acids, such as glycolic acid and lactic acid, are preferred in cosmetic compositions due to the AHAs ability to penetrate skin. In particular, the bioavailability of short chain AHAs stimulates cellular activity in the epidermis and dermis, as well as increases desquamation of the outer layers of the epidermis to help alleviate and treat the skin conditions above. Furthermore, short chain AHAs can aid and stimulate collagen synthesis, which further helps reduce rhytids, while improving skin elasticity and firmness.

However, a major problem with using AHAs in skin care compositions is the fact that AHAs are acids, which can lead to skin irritation. And while using AHAs for their acidic properties may be desirable in certain applications, such as for skin peel applications, the acidity of AHAs can have detrimental and undesirable effects for more daily and routine applications.

In order to reduce the irritation associated with using AHAs in skin care compositions, other compounds can be added in an attempt to make the overall skin care composition less acidic. For example, U.S. Pat. Nos. 5,886,042 and 5,385,938 discuss adding an amphoteric or pseudoamphoteric compound with the AHAs to try and raise the overall pH of the cosmetic composition. However, not only do these compositions require an additional component, such as amino acids and imidazoline compounds, which may not be desirable for a particular composition or use, but this strategy also does not address the underlying issue regarding the acidity of the AHAs. Rather, by attempting to balance the AHA with another compound, the acidity of the AHA is merely being masked and not reduced. By not addressing the problematic acidity of the AHAs, skin irritation and intolerability can persist, especially in users with sensitive skin.

In addition to problems associated with the acidity of AHAs, skin care compositions in the field generally have problems sustaining relatively long-term stability, while also allowing sufficient penetration of the active ingredient into the skin. Stability problems can occur based on a variety of environmental factors, including changes in temperature and humidity during processing, shipping, storage, and use, as well as chemical factors within the compositions, including the miscibility or homogeneity of the various components. In this respect, less stable compositions can be more acidic and can potentially become more acidic over time due to masking components becoming diminished or separating out of the compositions, which further exacerbates the irritability of the compositions.

Accordingly, there remains a need in the art for skin care compositions that have reduced acidity and potential irritability, while also having sufficient stability and penetration properties. As such, there remains a need in the art for skin care compositions having at least one cyclic diester, such as at least one cyclic diester of an AHA. Moreover, there remains a need in the art for skin care compositions having the aforementioned cyclic diester and at least one polar non-aqueous solvent.

SUMMARY OF THE INVENTION

The present invention generally relates to novel skin care compositions comprising:
(a) at least one cyclic diester of an alpha hydroxy acid; and
(b) at least one polar non-aqueous solvent;
wherein the composition comprises less than 1 wt. % of water.

In certain embodiments, the present invention relates to novel skin care compositions comprising:
(a) 0.1-60 wt. % of at least one cyclic diester of an alpha hydroxy acid; and
(b) 40-99.9 wt. % of at least one polar non-aqueous solvent having a polarity of about 5 to about 20;
wherein the composition comprises less than 1 wt. % of water.

Another embodiment of the present invention relates to a process for producing the novel skin care compositions.

BRIEF DESCRIPTION OF THE DRAWINGS

FIG. 1 represents the relative skin penetration of four exemplary skin care compositions versus a control of water, in which the layers are along the x-axis and the absorbance at 1766 cm−1 is along the y-axis.

DETAILED DESCRIPTION OF THE INVENTION

Definitions:

The term and phrases "invention," "present invention," "instant invention," and similar terms and phrases as used herein are non-limiting and are not intended to limit the present subject matter to any single embodiment, but rather encompass all possible embodiments as described.

As used herein, the term "about" means within 15% of the reported numerical value; in another embodiment, the term "about" means within 10% of the reported numerical value.

As used herein, the term "skin care composition," "cosmetic," "cosmetic composition," and similar terms, including plural terms, can be used interchangeably. Specifically, the term skin care composition includes compositions that can be rubbed, poured, sprinkled, or sprayed on, introduced into, or otherwise applied to the human body, including skin, or any part thereof for cleansing, beautifying, promoting attractiveness, or altering the appearance, as well as includes compositions intended for use as a component of another cosmetic. The term "skin care composition" and other terms above do not exclude soap, and specifically includes topical compositions for application to human skin.

As used herein, the terms "a," or in the alternative "the" when referencing a component already disclosed, and "at least one" shall have the same meaning and can be used interchangeably.

As used herein, all weight percentages (wt. %) are based on the total wt. % of the skin care composition, unless otherwise specified. Additionally, all composition percentages are based on totals equal to 100 wt. %, unless otherwise specified.

Skin Care Compositions:

The skin care compositions herein provide an alternative to other compositions having AHAs, while at the same time providing stable compositions having reduced acidity, including in preferred embodiments having low acidity, and good skin penetration.

As discussed above, while the use of AHAs has increased in the cosmetic industry due to the beneficial effects AHAs have on skin, a major drawback with using AHAs is the acidic nature of the compounds. For instance, glycolic acid and lactic acid, which are $C_2$ and $C_3$ AHAs respectively, both have pKa values less than 4. See, e.g., W. M. Haynes, *CRC Handbook of Chemistry and Physics* 5-94 to 5-95 (94th ed. 2013). This relatively high acidity can cause irritation and discomfort to the user, especially users with sensitive skin.

Surprisingly, it has been found that by using at least one cyclic diester of an alpha hydroxy acid, and at least one polar non-aqueous solvent, preferably at least two polar non-aqueous solvents, skin care compositions can be formed having very low acidity and good stability, while also allowing the cyclic diester to penetrate skin. Since the present skin care compositions have such low acidity, the irritation and discomfort associated with traditional compositions containing AHAs can be minimized or prevented. Additionally, since the instant invention provides a way for the cyclic diester to penetrate the skin upon topical application, the benefits associated with the cyclic diesters and corresponding AHAs can be obtained by the user.

In order to reduce the irritation and discomfort associated with compositions having AHAs, generally in preferred embodiments, the skin care compositions can have a pH of 5.5 to 8, more preferably 6 to 8, and even more preferably the skin care compositions can have a pH of about 7. Alternatively, the skin care compositions can be formulated with other components to have a lower pH, including a pH of 3 to 8, more preferably 3.5 to 7, and even more preferably 3.8 to 4.2.

Moreover, in addition to the pH, in preferred embodiments the skin care compositions can have an acidity of 2 wt. % or less, more preferably 1.5 wt. % or less, at about 20° C. In other embodiments, the skin care compositions can have an acidity of 1 wt. % or less at about 20° C. The acidity of the skin care compositions can be determined by the amount of cyclic ester in the skin care composition that has converted into another form and is not in the cyclic form. Specifically, the acidity of the skin care compositions can be determined by the amount of cyclic ester that has converted into an acidic, non-cyclic dimer form and the amount of cyclic ester that has converted into the corresponding free form AHAs, as well as any AHAs that may have been added to the compositions.

The current skin care compositions also allow cyclic diesters of an alpha hydroxy acid, or mixtures of cyclic diesters, to penetrate skin. In particular embodiments, the skin care compositions can improve the penetration of at least one cyclic diester of an alpha hydroxy acid through at least one layer of skin by at least 20%, preferably at least 40%, more preferably at least 60%, and even more preferably at least 80% versus skin care compositions not having at least one polar non-aqueous solvent.

Furthermore, in certain embodiments, the skin care compositions can provide an absorbance of at least 0.1, preferably at least 0.2, more preferably at least 0.3 for at least one skin layer determined by attenuated total reflectance (ATR)-FTIR spectroscopy at 1766 cm−1. In particularly preferred embodiments, the skin care compositions can provide an absorbance of about 0.1 to about 1.5, preferably about 0.15 to about 1.0, and more preferably about 0.2 to about 0.8 for at least one skin layer determined by attenuated total reflectance (ATR)-FTIR spectroscopy at 1766 cm−1.

Cyclic Diesters of an Alpha Hydroxy Acid:

The cyclic diester that can be used in the invention can be any cyclic diester of any alpha hydroxy acid. In preferred embodiments, the cyclic diester is a $C_4$-$C_8$ diester, which can be formed from the dimerization of two $C_2$-$C_4$ AHAs. In this respect, the cyclic diester can be a cyclic dimer of two identical AHAs, or a combination of two different AHAs. For example, the cyclic diester can be formed by two glycolic acid molecules resulting in glycolide, two lactic acid molecules to form lactide, or one glycolic acid and one lactic acid molecule. Additionally, all isomers of the AHAs are encompassed, including all isomers of lactide, such as the D- and L-isomers.

In certain embodiments, the cyclic diester can have the following formula:

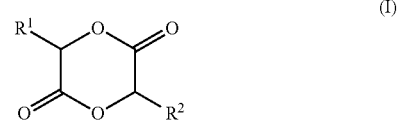

wherein $R^1$ is hydrogen or a $C_1$-$C_2$ alkyl, alkenyl, or alkynyl; and $R^2$ is hydrogen or a $C_1$-$C_2$ alkyl, alkenyl, or alkynyl. In preferred embodiments, the cyclic diester can have formula (I) wherein $R^1$ is hydrogen, methyl, or ethyl; and $R^2$ is hydrogen, methyl, or ethyl. In a more preferred embodiment, the cyclic diester can be glycolide or lactide, in which $R^1$ and $R^2$ are both hydrogen or methyl, respectively.

Additionally, while the cyclic diester can be in a single chemical form, for example, glycolide or lactide, the skin care compositions of the instant invention can also have mixtures of various cyclic diesters. In particular, the skin care compositions can have mixtures of $C_4$-$C_8$ diesters, including but not limited to mixtures of glycolide and lactide.

With respect to the amount of cyclic diester in current skin care compositions, preferably the compositions can comprise 0.1 to 60 wt. %, including 0.1 to 50 wt. %, of at least one cyclic diester of an alpha hydroxy acid. In more preferred embodiments, the skin care compositions can comprise 0.5 to 25 wt. %, including 1 to 20 wt. %, and more preferably 1 to 10 wt. % of at least one cyclic diester. In specifically preferred embodiments, the skin care compositions can comprise 0.1 to 50 wt. %, including 0.5 to 25 wt. %, and more preferably 1 to 20 wt. %, including 1 to 10 wt. %, of glycolide, lactide, or combinations thereof. In embodiments having mixtures of cyclic diesters, preferably the skin care compositions can have about 0.1 to 30 wt. %, more preferably 1 to 20 wt. %, including 1 to 10 wt. %, of glycolide. In other embodiments having mixtures of cyclic diesters, preferably the skin care compositions can have about 0.1 to 30 wt. %, more preferably 1 to 20 wt. %, including 1 to 10 wt. %, of lactide.

Polar Non-Aqueous Solvents:

Various polar non-aqueous solvents can be used in the instant skin care compositions. In certain embodiments, the skin care compositions can have at least one polar non-aqueous solvent, and in certain preferred embodiments, the skin care compositions can have at least two polar non-aqueous solvents.

Specifically, at least one polar non-aqueous solvent in the instant skin care compositions should be able to dissolve a cyclic diester of an alpha hydroxy acid to some degree. In this respect, in preferred embodiments, the polar non-aqueous solvent can dissolve at least 1 wt. %, more preferably at least 5 wt. %, and even more preferably at least 10 wt. % of the cyclic diester based on the weight of the solvent in the skin care composition. In particularly preferred embodiments, at least one polar non-aqueous solvent can dissolve 1 to 20 wt. %, more preferably 5 to 20 wt. %, and even more preferably 10 to 20 wt. % of the cyclic diester based on the weight of the solvent in the skin care composition.

Moreover, the polar non-aqueous solvent can be any organic solvent. In certain embodiments, the polar non-aqueous solvent can be a polar $C_1$-$C_{15}$ solvent, more preferably the solvent can be a polar $C_1$-$C_{10}$ solvent, and even more preferably the solvent can be a polar $C_2$-$C_{10}$ solvent. Specifically, the polar non-aqueous solvent can have a polarity of at least 5, and in certain preferred embodiments, the polar non-aqueous solvent can have a polarity of at least 8, as defined in C. M. Hansen, *Hansen Solubility Parameters: A User's Handbook* (2nd ed. 2007) ("Hansen"), which is incorporated herein by reference in its entirety. Further, in certain embodiments, the polar non-aqueous solvent can have a polarity of about 5 to about 20, and more preferably about 8 to about 18, as defined in Hansen.

In addition to polarity, the non-aqueous solvents can have a certain hydrogen bonding potential, as defined in Hansen. In preferred embodiments, the polar non-aqueous solvent can have a hydrogen bonding potential of at least 5 up to about 30, and more preferably at least 5 up to about 25, and even more preferably at least 5 up to about 20, as defined in Hansen. In particularly preferred embodiments, the polar non-aqueous solvent can have a hydrogen bonding potential of at least 5 up to about 25, and a polarity of at least 5 up to about 20, as defined in Hansen. Even more preferred embodiments can have a hydrogen bonding potential of about 6 to about 10, and can have a polarity of about 7 to about 11, as defined in Hansen.

With respect to the chemical structure, the polar non-aqueous solvent can be substituted or unsubstituted, and can be linear, branched, or cyclic, including bicyclic, aromatic, or both. If the solvent is cyclic, including bicyclic, aromatic, or both, the solvent can have at least one heteroatom in the cyclic structure, including but not limited to oxygen, nitrogen, or combinations thereof. Additionally, while the polar non-aqueous solvent is not limited to having any particular functional group(s), in preferred embodiments, the polar non-aqueous solvent can have at least one carbonyl, ether, alcohol, amide, amine, imine, cyanate, isocyanate, nitrile, isonitrile, and combinations thereof.

In certain embodiments, the skin care compositions can have at least one polar non-aqueous solvent of formula (II):

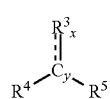
(II)

wherein $R^3$ is hydrogen, oxygen, ether, or ester; $R^4$ is hydrogen or an alkyl, alkenyl, alkynyl, or alkyl hydroxy group; $R^5$ is nitrogen, an alkyl, hydroxyl, ether, ester, amide, or amine; $R^6$ is an alkyl, ether, ester, amide, amine, or combinations thereof; and x is 0 or 1; with the proviso that if $R^5$ is nitrogen and forms a nitrile group, then x is 0, and if $R^3$ is oxygen, then $C_y$ and $R^3$ form a carbonyl; wherein $R^4$ and $R^5$ can join to form a cyclic or bicyclic structure including an aromatic structure, which can include heteroatoms and can be optionally substituted with at least one $R^6$ group. If formula (II) has more than one $R^6$ group, the $R^6$ groups can be the same or different. Preferably, $R^3$ is oxygen to form a carbonyl with $C_y$, or a $C_1$-$C_5$ alkoxy or aryloxy group; $R^4$ is hydrogen or a $C_1$-$C_5$ alkyl; and $R^5$ is nitrogen, a $C_1$-$C_5$ alkyl, a $C_1$-$C_5$ ether, a $C_1$-$C_5$ ester, or an amide; with the proviso that if $R^5$ is nitrogen and forms a nitrile group, then x is 0.

Alternatively, in other preferred embodiments, the skin care compositions can have at least one polar non-aqueous solvent of formula (III), formula (IV), or mixtures thereof:

(III)

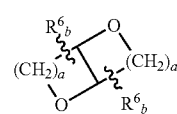
(IV)

wherein $R^6$ is an alkyl, ether, ester, amide, amine, or combinations thereof; a is 1 to 3; b is 1 to 5; and z is 1 to 3. Preferably, $R^6$ is a $C_1$-$C_5$ alkoxy group, $C_1$-$C_5$ aryloxy group, or combinations thereof, and more preferably $R^6$ is a methoxy, ethoxy, or combinations thereof. Further, in preferred embodiments, b is 1 to 4, and more preferably 1 to 3.

In particularly preferred embodiments, the polar non-aqueous solvent can be polar $C_1$-$C_{10}$ alcohols, including diols, ketones, esters, ethers, cyclic ethers, amides, nitriles, and mixtures thereof, and specifically includes polar $C_1$-$C_5$ linear or branched, substituted or unsubstituted ketones, esters, ethers, amides, nitriles, and mixtures thereof. Additionally, the polar non-aqueous solvent specifically includes polar $C_4$-$C_{10}$ cyclic ethers, cyclic ketones, and mixtures thereof, which can be substituted or unsubstituted. Moreover, the polar non-aqueous solvent can be a mixture of solvents of formula (II), (III), and/or (IV). In particular embodiments, the non-aqueous solvent can be blends of the polar $C_1$-$C_5$ linear or branched, substituted or unsubstituted ketones, esters, ethers, amides, nitriles, and mixtures thereof, with the polar, substituted or unsubstituted $C_4$-$C_{10}$ cyclic ethers, cyclic ketones, and mixtures thereof.

Non-limiting examples of particularly preferred embodiments of the polar non-aqueous solvent can include dimethylacetamide, acetonitrile, ethyl acetate, tetrahydrofuran, dimethylformamide, methyl ethyl ketone, cyclohexanone, isosorbide dimethyl ether (also known as "dimethyl isosorbide"), methanol, ethanol, propanol, isopropanol, propylene glycol, and mixtures thereof.

The current skin care compositions can comprise 40 to 99.9 wt. %, including 50 to 99.9 wt. %, of at least one polar non-aqueous solvent, and more preferably can comprise 75 to 99.5 wt. %, even more preferably 80 to 99 wt. %, of the polar non-aqueous solvent. As previously indicated, the polar non-aqueous solvent can include mixtures of solvents, including mixtures of at least two polar non-aqueous solvents, the mixtures having a final weight percent according to the ranges above based on the total weight percentage of the composition.

Other Components:

Other active cosmetic compounds, active pharmaceutical compounds, or mixtures thereof, may be included in the instant skin care compositions. Non-limiting examples can include compounds that improve or eradicate age spots, keratosis, and wrinkles; exfoliates, analgesics; anesthetics; antiacne agents; antibacterials; antiyeast agents; antifungal agents; antiviral agents; antidandruff agents; antidermatitis agents; antipruritic agents; antiemetics; antiinflammatory agents; antihyperkeratolytic agents; moisturizers; antiperspirants; antipsoriatic agents; antiseborrheic agents; hair conditioners and hair treatment agents; antiaging agents; antiasthmatic agents and bronchodilators; sunscreen agents; antihistamine agents; skin lightening agents; depigmenting agents; vitamins; corticosteroids; tanning agents; hormones; retinoids; topical cardiovascular agents, and other dermatologicals.

Generally, other active components may be present up to about 15 wt. %, preferably up to about 10 wt. %, and more preferably up to about 5 wt. %. More specifically, the instant skin care compositions can have 0 to 15 wt. %, preferably 0 to 10 wt. %, and even more preferably 0 to 5 wt. % of additional active components.

Moreover, while the skin care compositions can have water present, in preferred embodiments, the compositions can have less than 1 wt. %, more preferably 0.5 wt. % or less, even more preferably 0.25 wt. % or less, and most preferably 0.1 wt. % or less of water. In particularly preferred embodiments, the skin care compositions can be relatively anhydrous with no water present up to less than 1 wt. %, more preferably less than 0.5 wt. %, even more preferably less than 0.1 wt. %, including residual water. In this respect, the skin care compositions can have at least one water scavenger, including, but not limited to fumed silica, aluminosilicate, aluminum silicate, including magnesium aluminum silicate, aluminum starch octenylsuccinate, and combinations thereof. The water scavenger can be present up to about 15 wt. %, preferably up to about 10 wt. %, and more preferably up to about 5 wt. %.

Various surfactants, emulsifiers, gelling agents, stabilizers, plasticizers, rheology agents, and combinations thereof, can be added to the instant skin care compositions. Specifically, as a non-limiting example, at least one surfactant can be added to homogenize the skin care compositions. The surfactants, emulsifiers, gelling agents, stabilizers, plasticizers, rheology agents, and combinations thereof, can be present up to about 15 wt. %, and preferably up to about 10 wt. %.

In addition to the cyclic diesters, the skin care compositions can have AHAs present. While the amount of the AHAs can generally be less than the amount of the cyclic diesters, the instant compositions can have up to about 5 wt. % of AHAs present, more preferably up to about 2 wt. % of AHAs present, and even more preferably up to about 1 wt. % of AHAs present. Specifically preferred AHAs can include glycolic acid, lactic acid, or combinations thereof. Further, if AHAs are present in the skin care compositions, the AHAs can be added to the compositions in addition to the cyclic diesters, or the AHAs can be produced by the hydrolyzation of the cyclic diesters of the alpha hydroxy acids. However, in order to minimize the potential irritability of the skin care compositions, and within the general pH and acidity ranges indicated above for the compositions, the amount of AHAs present, either as an added component or from hydrolysis of the cyclic diester, should be relatively low and in accordance with the ranges above.

Besides the other active compounds, other inactive compounds such as, but not limited to colorants, fragrances, abrasive compounds, including silica dioxide, polymeric resins, clays, and combinations thereof can be added to the skin care compositions. Generally, the inactive components may be present up to about 5 wt. %, preferably up to about 2.5 wt. %, and more preferably up to about 1 wt. %. More specifically, the instant skin care compositions can have 0 to 5 wt. %, preferably 0 to 2.5 wt. %, and even more preferably 0 to 1 wt. % of the inactive compounds.

Method of Making the Skin Care Compositions:

The current skin care compositions can be made in a variety of ways, including in a continuous process or in a batch process. For example, as a non-limiting example, all of the components, including at least one cyclic diester of an alpha hydroxy acid and at least one polar non-aqueous solvent, can be added together at the same time in the amounts previously indicated. Alternatively, as another non-limiting example, certain components, such as at least one cyclic diester and at least one polar non-aqueous solvent can be added together first, with other components, including additional cyclic diester(s), polar non-aqueous solvent(s), or both, added subsequently.

In certain embodiments, the skin care compositions can be made by adding at least one cyclic diester of an alpha hydroxy acid and at least one polar non-aqueous solvent together to form a substantially homogenous mixture. In this respect, the substantially homogenous mixture can have less than 5 wt. %, more preferably less than 1 wt. %, even more preferably less than 0.5 wt. %, and most preferably less than 0.1 wt. % of the cyclic diester of an alpha hydroxy acid and/or the polar non-aqueous solvent in a separate phase than the mixture.

In addition to the method used to add together the various components of the skin care compositions, including a cyclic diester of an alpha hydroxy acid and at least one polar non-aqueous solvent, the components can be heated to make a substantially homogenous mixture. Specifically, as a non-limiting example, the cyclic diester and polar non-aqueous solvent can be heated to a temperature below the boiling point of the solvent. In other non-limiting embodiments, at least one polar non-aqueous solvent can be heated to a temperature below the boiling point of the solvent, and then the cyclic diester can be added to the solvent.

EXAMPLES

The following examples are illustrative of preferred skin care compositions and are not intended to be limitations thereon. All numerical values given are in weight percentage, and all product composition percentages are based on totals equal to 100% by weight, unless otherwise specified.

Test Methods:

Acidity Test:

The acidity test determined the amount of acid formation in a tested example and was performed by titration. A Mettler Toledo DL58 Titrator apparatus equipped with a Mettler Toledo DM140-SC electrode was used to perform the potentiometric titration to determine the acidity of the tested example. The titrant consisted of 71 wt. % of toluene, 19 wt. % of methanol, and 10 wt. % of 1N tetrabutylammonium hydroxide. The titration was run at room temperature, which means at about 20° C. The acid formation results are reported as the weight percentage of acid from the conversion of glycolide or lactide into the acidic, non-cyclic dimer form and glycolic acid or lactic acid, respectively. The weight percentage of acid is calculated based on the molecular weight of glycolic acid or lactic acid, respectively.

Aging Test:

The aging test simulates storage stability. Each example tested was split into a room temperature sample ("R.T.") and an aged sample ("Aged"). The aged samples were placed in a VWR 1410 oven at 54° C. for fourteen (14) days, after which the aged samples were removed from the oven and tested for the amount of acid formation using the Acidity Test. The room temperature samples were tested without oven aging for the amount of acid formation using the Acidity Test.

Skin Penetration Test:

The skin penetration test determined the deposition, penetration, and conversion of the tested cyclic ester into the corresponding alpha hydroxy acids in the outer layers of ex vivo porcine skin by using attenuated total reflectance (ATR)-FTIR spectroscopy and tape stripping. The resulting absorbance reported was determined at 1766 cm−1. The FTIR spectrometer used was a Nicolet 700 FT-IR from Thermo Electron Corporation. Scotch® Magic™ Tape was used for the tape stripping, which is available from 3M, St. Paul, Minn., USA.

Procedure:

Step 1: A sample of porcine skin was washed with water;
Step 2: The porcine skin was then scanned using ATR-FTIR as the control ("Control Layer");
Step 3: Each composition that was tested, as indicated below in the tables, was then applied to the porcine skin and allowed to stand for two (2) hours at 34° C.;
Step 4: After two (2) hours, the excess composition was removed from the surface of the porcine skin;
Step 5: The porcine skin was then scanned by ATR-FTIR as the surface ("Surface Layer");
Step 6: A strip of tape was then evenly applied to the treated area on the porcine skin;
Step 7: The strip of tape was then removed from the porcine skin;
Step 8: The porcine skin was then scanned by ATR-FTIR monitoring the absorbance at 1766 cm-1, and recording the result as "Skin Layer 1"; and
Step 9: Steps 3-8 were repeated nine (9) more times, which each subsequent scanned skin layer numbered accordingly. In particular, skin layers 1-10 correspond to the number of times a strip of tape was applied to and removed from the skin sample, and the skin sample was scanned by ATR-FTIR.

Materials:

"DMI" is dimethyl isosorbide, also known as isosorbide dimethyl ether, which is available from Grant Industries Inc., Elmwood Park, N.J., USA.

"EtOH" is ethanol, which is available from Macron Chemicals, Center Valley, Pa., USA.

"Glycolic Acid" is DuPont™ Glypure® glycolic acid, which is available from E. I. Du Pont de Nemours & Co. Inc., Wilmington, Del., USA.

"Glycolide" is a $C_4$ cyclic diester formed from glycolic acid having a purity of at least 99 wt. %.

"Lactide" is L-Lactide, which is available from TCI Tokyo Chemical Industry Co., Ltd, Tokyo, Japan.

"PG" is propylene glycol, which is available from J. T Baker, Phillipsburg, N.J., USA.

"Water" is deionized water.

Example 1

A 100 g skin care composition was prepared by adding 89 g of ethanol, 10 g of polypropylene glycol, and 1 g of glycolide into a mixing container and mixing the components together using a magnetic stirrer until a homogenous mixture was obtained.

The homogenous mixture was then tested for acidity, the results of which are reported in Table 1.

Example 2

A 100 g skin care composition was prepared in the same manner as Example 1, with the exception that the ethanol was not dried before being mixed with the polypropylene glycol and glycolide.

Comparative Example 1

A 100 g comparative composition was prepared in the same manner as Example 1, with the exceptions that 1 g of water was added to the ethanol, polypropylene glycol, and glycolide, and 88 g of ethanol was used.

Comparative Example 2

A 100 g comparative composition was prepared in the same manner as Example 1, with the exceptions that 5 g of water was added to the ethanol, polypropylene glycol, and glycolide, and 84 g of ethanol was used.

TABLE 1

| Ingredient (wt. %) | Example 1 | Example 2 | Comp. Ex. 1 | Comp. Ex. 2 |
|---|---|---|---|---|
| EtOH | 89 | 89 | 88 | 84 |
| PG | 10 | 10 | 10 | 10 |
| Glycolide | 1 | 1 | 1 | 1 |
| Water | — | — | 1 | 5 |
| R.T.-Acid Formation % | 1.4 | 1.9 | 4.3 | 9.9 |
| Aged-Acid Formation % | 1.5 | 2.0 | 5.2 | 14.3 |

Example 3

A 100 g skin care composition was prepared in the same manner as Example 1, with the exception that 1 g of lactide was used instead of 1 g of glycolide. The homogenous mixture was then tested for acidity, the results of which are reported in Table 2.

Comparative Example 3

A 100 g comparative composition was prepared in the same manner as Comparative Example 1, with the exception that 1 g of lactide was used instead of 1 g of glycolide.

Comparative Example 4

A 100 g comparative composition was prepared in the same manner as Comparative Example 2, with the exception that 1 g of lactide was used instead of 1 g of glycolide.

TABLE 2

| Ingredient (wt. %) | Example 3 | Comp. Ex. 3 | Comp. Ex. 4 |
|---|---|---|---|
| EtOH | 89 | 88 | 84 |
| PG | 10 | 10 | 10 |

TABLE 2-continued

| Ingredient (wt. %) | Example 3 | Comp. Ex. 3 | Comp. Ex. 4 |
|---|---|---|---|
| Lactide | 1 | 1 | 1 |
| Water | — | 1 | 5 |
| R.T.-Acid Formation % | 0.8 | 1.4 | 7.0 |
| Aged-Acid Formation % | 0.1 | 2.1 | 6.9 |

Example 4

A 100 g skin care composition was prepared by adding 90 g of dimethyl isosorbide and 10 g of glycolide into a mixing container and mixing the components together using a magnetic stirrer until a homogenous mixture was obtained.

The homogenous mixture was then tested for acidity, the results of which are reported in Table 3.

Comparative Example 5

A 100 g comparative skin care composition was prepared in the same manner as Example 4, with the exception that 10 g of glycolic acid was used instead of 10 g of glycolide.

TABLE 3

| Ingredient (wt. %) | Example 4 | Comp. Ex. 5 |
|---|---|---|
| DMI | 90 | 90 |
| Glycolide | 10 | — |
| Glycolic Acid | — | 10 |
| R.T.-Acid Formation % | 0.5 | 101.1 |
| Aged-Acid Formation % | 0.0 | 88.1 |

Example 5

A 100 g skin care composition was prepared by adding 99 g of dimethyl isosorbide and 1 g of glycolide into a mixing container and mixing the components together using a magnetic stirrer until a homogenous mixture was obtained.

The homogenous mixture was then tested for skin penetration, the results of which are reported in Table 4.

Example 6

A 100 g skin care composition was prepared in the same manner as Example 5, with the exceptions that 95 g of dimethyl isosorbide and 5 g of glycolide was used instead of 99 g of dimethyl isosorbide and 1 g of glycolide, respectively.

Example 7

A 100 g skin care composition was prepared in the same manner as Example 5, with the exceptions that 90 g of dimethyl isosorbide and 10 g of glycolide was used instead of 99 g of dimethyl isosorbide and 1 g of glycolide, respectively.

Example 8

A 100 g skin care composition was prepared in the same manner as Example 5, with the exceptions that 85 g of dimethyl isosorbide and 15 g of glycolide was used instead of 99 g of dimethyl isosorbide and 1 g of glycolide, respectively.

TABLE 4

| Ingredient (wt. %) | Control | Example 5 | Example 6 | Example 7 | Example 8 |
|---|---|---|---|---|---|
| DMI | — | 99 | 95 | 90 | 85 |
| Glycolide | — | 1 | 5 | 10 | 15 |
| Water | 100 | — | — | — | — |
| Control Layer | 0.08 | 0.1 | 0.09 | 0.07 | 0.1 |
| Surface Layer | 0.05 | 0.15 | 0.43 | 0.65 | 1.39 |
| Skin Layer 1 | 0.05 | 0.11 | 0.27 | 0.42 | 0.76 |
| Skin Layer 2 | 0.07 | 0.11 | 0.12 | 0.29 | 0.68 |
| Skin Layer 3 | 0.05 | 0.09 | 0.15 | 0.18 | 0.27 |
| Skin Layer 4 | 0.04 | 0.11 | 0.12 | 0.14 | 0.3 |
| Skin Layer 5 | 0.05 | 0.09 | 0.13 | 0.12 | 0.24 |
| Skin Layer 6 | 0.05 | 0.06 | 0.12 | 0.12 | 0.24 |
| Skin Layer 7 | 0.05 | 0.07 | 0.14 | 0.1 | 0.2 |
| Skin Layer 8 | 0.06 | 0.06 | 0.12 | 0.11 | 0.26 |
| Skin Layer 10 | 0.07 | 0.07 | 0.13 | 0.12 | 0.18 |

The skin penetration of Examples 5-8 are shown above in Table 4 and illustrated in FIG. 1. The absorbance for each skin layer was determined at 1766 cm-1, which is a region where glycolide absorbs well, while the non-cyclic dimer and glycolic acid absorb less. Accordingly, a skin layer demonstrating a higher absorbance value at 1766 cm-1 correlates to a higher concentration of glycolide at that skin layer. In this respect, the skin penetration properties can be determined by measuring the concentration of glycolide at various skin layers.

Examples 5-8 all generally show significantly better skin penetration properties versus the control. Additionally, Examples 5-8 demonstrate improved skin penetration properties of glycolide in the first several skin layers, especially as the glycolide concentration increased. Even in deeper skin layers, glycolide penetration can be significantly improved, as demonstrated by Examples 6-8.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A skin care composition comprising:
   (a) 0.1-50 wt. % of at least one cyclic diester of an alpha hydroxy acid; and
   (b) 50-99.9 wt. % of isosorbide dimethyl ether; wherein the composition comprises less than 1 wt. % of water.

2. The skin care composition of claim 1, wherein the cyclic diester is a C4-C8 diester dimer of two C2-C4 alpha hydroxy acids.

3. The skin care composition of claim 1, wherein the cyclic diester is glycolide, lactide, or mixtures thereof.

4. The skin care composition of claim 1 comprising 1-20 wt. % of the cyclic diester.

5. The skin care composition of claim 1 comprising 80-99 wt. % of the isosorbide dimethyl ether.

6. The skin care composition of claim 1 comprising 0.5 wt. % or less of water.

7. A method of making a skin care composition having at least one cyclic diester of an alpha hydroxy acid and isosorbide dimethyl ether, the method comprising mixing:
   (a) 0.1-50 wt. % of the at least one cyclic diester of an alpha hydroxy acid; and (b) 50-99.9 wt. % of the isosorbide dimethyl ether, to form a mixture; wherein the composition comprises less than 1 wt. % of water.

* * * * *